US00PP11650P

United States Patent [19]

Ogilvie

[11] Patent Number: Plant 11,650

[45] Date of Patent: Nov. 28, 2000

[54] SHRUB ROSE PLANT NAMED 'AC MARIE-VICTORIN'

[75] Inventor: Ian S. Ogilvie, Pointe Claire, Canada

[73] Assignee: Her Majesty the Queen in right of Canada, as represented by the Minister of Agriculture, Ontario, Canada

[21] Appl. No.: 09/189,941

[22] Filed: Nov. 12, 1998

[51] Int. Cl.[7] ..... A01H 5/00

[52] U.S. Cl. ..... Plt./107

[58] Field of Search ..... Plt./107, 102, 141, Plt./148

[56] References Cited

PUBLICATIONS

Ogilvie, et al., 1999, "Three New Winter–Hardy Explorer Rose Cultivars", Hortscience 34(2):358–360. (Dialog (R) File 50: CAB Abstracts).

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms in clusters attractive peach-pink blossoms that tend to lighten somewhat when fully open. The new variety exhibits a large arching growth habit with medium green foliage that exhibits strong glossiness on the upper surface, and good winter hardiness. The blossoms are round when viewed from above and are somewhat flattened when viewed from the side. Good resistance to powdery mildew has been observed. The leaflets commonly number seven per leaf. The new variety propagates well by the use of softwood stem cuttings, and is well adapted for growing as ornamentation in the landscape.

2 Drawing Sheets

SUMMARY OF THE INVENTION

The new *Rosa hybrida* variety of shrub rose plant of the present invention was created during 1985 by artificial pollination at the Central Experimental Farm, Ottawa, Ontario, Canada. The female parent (i.e., the seed parent) was the 'Arthur Bell' variety (non-patented in the United States) and the male parent (i.e., the pollen parent) was the 'John Davis' floribunda variety (non-patented in the United States). Each parent had been previously studied in the hope that it would contribute the desired attractive characteristics to the product of the cross. Following observation of the offspring of this cross a single plant of the new variety was observed and selected.

The parentage of the new variety can be summarized as follows:

'Arthur Bell'×'John Davis'.

It was found that the new variety of shrub rose plant of the present invention possesses the following combination of characteristics:

(a) exhibits a large arching growth habit with attractive medium green foliage that bears strong glossiness on the upper surface,
(b) forms in clusters attractive peach-pink blossoms that tend to lighten when fully mature,
(c) propagates well by the use of softwood cuttings,
(d) exhibits good winter hardiness,
(e) exhibits good resistance to powdery mildew, and
(f) is particularly well suited for growing as ornamentation in the landscape.

The rose plants of the new variety can be grown well on their own roots out-of-doors without protection at L'Assomption, Quebec, Canada. The blossoms commonly appear continuously for approximately ten weeks beginning in mid-June. Resistance to powdery mildew and moderate resistance to blackspot has been observed to date.

When compared to 'Simon Fraser' variety (U.S. Plant Pat. No. 9,178), the new variety of the present invention exhibits a larger arching growth habit unlike the smaller upright bushy growth habit of the 'Simon Fraser' variety, forms generally larger blossoms that are a paler pink, and commonly forms seven leaflets per leaf as opposed to three or five leaflets per leaf.

The new variety well meets the needs of the horticultural industry. It can be grown to advantage as attractive ornamentation in parks, gardens, public areas, and residential landscapes.

The characteristics of the new variety have been found to be homogenous and stable and have been shown to be strictly transmissible by asexual propagation by the rooting of softwood stem cuttings conducted at L'Assomption, Quebec, Canada, beginning in 1985.

The new variety has been named 'AC Marie-Victorin'. Also, the new variety is a member of the EXPLORER Series of hardy rose plants.

BRIEF DESCRIPTION OF THE PHOTOGRAPHS

The accompanying photographs show, as nearly true as it is reasonably possible to make the same in color illustrations of this character, typical specimens of mature plants and plant parts of the new variety. The illustrated rose plants of the new variety were photographed during 1995 while growing on their own roots at L'Assomption, Quebec, Canada.

FIG. 1—illustrates a typical flowering plant of the new variety while growing in the landscape. The arching growth habit, abundant medium green glossy foliage, and large double peach-pink blossoms are apparent.

FIG. 2—illustrates typical specimens of the blossoms at various stages in their maturity wherein some fading of the blossoms coloration is apparent with advancing age. The glossy medium green foliage also is shown.

DETAILED DESCRIPTION

The chart used in the identification of colors is that of The Royal Horticultural Society (R.H.S. Colour Chart). Common color terms are to be accorded their ordinary dictionary significance. The description is based on the observation of mature plants of the new variety while being grown outdoors at L'Assomption, Quebec, Canada.

Class: Shrub.

Plant:

*Height.*—A mature plant commonly assumes a height of approximately 1 m. and a width of approximately 1.25 m. at the end of the growing season.

*Habit.*—Arching.

Thorns:

*Quantity.*—Variable with typically 0 to 9 per 10 cm. of stem.

*Size.*—Medium with the sparse presence of short (<5 mm.) and long (>5 mm.) thorns.

*Color.*—Green Group 143D.

*Configuration.*—Deep concave.

Leaves: Compound and pinnate.

*Petiole.*—Green group 143C on upper surface and green group 143D on under surface.

*Stipule.*—Green group 143C to 143D in coloration.

Figure 1:
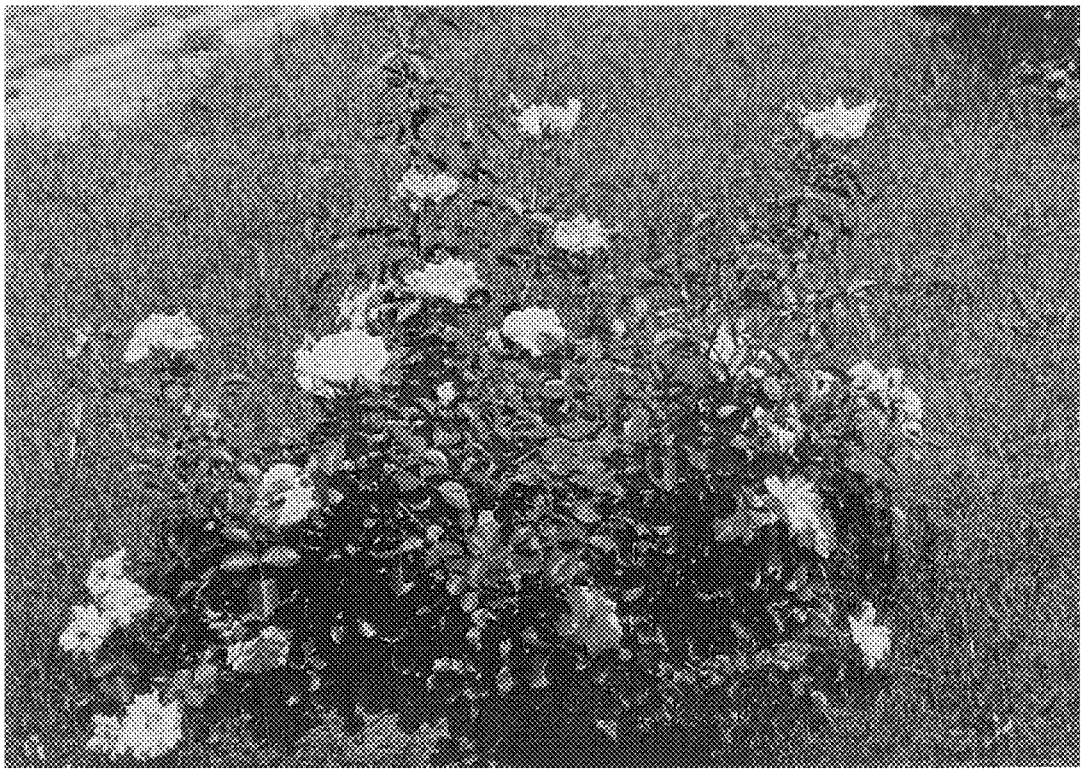
Figure 2:
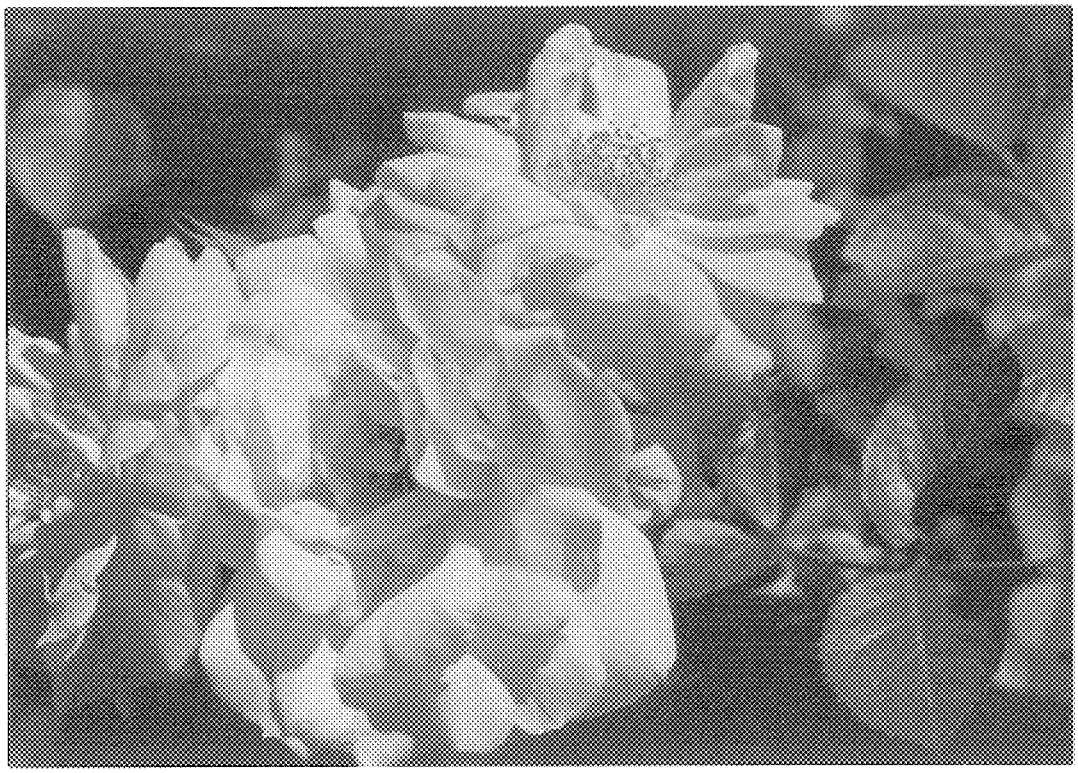

*Leaflets.*—Number: 3, 5, and 7 (most often). Shape: Elliptic and acuminate (as illustrated in FIG. 2) with a somewhat cordate base. Margins: Serrate. Size: Commonly approximately 100 to 140 mm. (120.5 mm. mean) in length and approximately 75 to 95 mm. (83.5 mm. mean) in width on average. Texture: Leathery. General appearance: Medium green with strong glossiness on upper surface.

*Color.*—Adult foliage: Medium green, Yellow-Green Group 147A on upper surface and Yellow-Green Group 147A on under surface. Young foliage: Lighter green, Green Group 143A an upper surface and Green Group 143C on under surface. Young shoots: Bear strong anthocyanin coloration.

Inflorescence:

*Number of flowers.*—Commonly approximately 4 to 14 per shoot.

*Pedicel.*—Commonly bears a medium number of thorns, and Green Group 143B in coloration.

*Sepals.*—With weak extensions, and commonly approximately 16 to 25 mm. (19.9 mm. mean) in length. The coloration varies from Yellow-Green Group 144B to 147C on the upper surface and from Yellow-Green Group 144A to 144B on the under surface.

*Buds.*—Shape: Pointed in longitudinal section. Color upon opening: Blend of rose and orange, Red Group 55A upon opening, and Red-Purple Group 58B on the upper surface and Red Group 55A on the under surface.

*Flower.*—Shape: Round when viewed from above and tend to flatten with maturity as viewed from the side. Diameter: Commonly approximately 70 to 84 mm. (75.9 mm. mean). Diameters of 85 to 90 mm have also been observed under different growing conditions. Color (when blooming): The overall blossom coloration initially is Red Group 55C, and when open the upper petal surface is Red Group 56A and under petal surface is Red Group 56C. The coloration of the blossoms commonly fades to a paler rose, Red Group 56D, when the blossoms are fully mature. The petals have a medium-sized yellow spot at the base that initially is Yellow Group 10B and on the upper surface and Yellow Group 10D on the under surface.

*Petal configuration.*—Possess weak reflexing and medium undulation.

*Fragrance.*—Weak.

*Petal number.*—Approximately 34 to 42 on average.

*Filaments.*—Yellow in coloration.

*Style.*—Short, and yellow-green in coloration with medium pubescence on the upper one half.

*Pollen.*—Bright yellow and abundantly formed.

*Stigma.*—Commonly disposed below the anthers.

*Petal drop.*—Petals commonly do not detach cleanly.

*Receptacle.*—Small and pear-shaped with prickles.

*Lasting quality.*—A blossom commonly lasts approximately 7 days on the plant.

*Duration.*—Blossoms commonly are formed beginning in mid-season (e.g., approximately June 15th) continuously over a period of 10 weeks or more when grown in the landscape.

*Hips.*—Round and orange in coloration.

Development:

*Blossoming.*—Continuous.

*Hardiness.*—Has survived winter temperatures of −35° C. to −40° C.

*Resistance to diseases.*—Is resistant to powdery mildew [*Sphaerotheca pannosa* (Wallr. ex Fr.) Lev.] and is moderately resistant blackspot (*Diplocarpon rosae* Wolf.) during observations to date.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products. Bramalea, Ontario, Canada) and placed under mist for 3 to 4 weeks at 20 to 25° C. ambient temperature. Tissue culture and grafting also can be utilized. However, the later is not recommended for optimum hardiness.

I claim:

1. A new and distinct variety of shrub rose plant characterized by the following combination of characteristics:

(a) exhibits a large arching growth habit with attractive medium green glossy foliage that bears strong glossiness on the upper surface,
(b) forms in clusters attractive peach-pink blossoms that tend to lighten when fully mature,
(c) propagates well by the use of softwood cuttings,
(d) exhibits good winter hardiness,
(e) exhibits good resistance to powdery mildew, and
(f) is particularly well suited for growing as ornamentation in the landscape;

substantially as herein shown and described.

* * * * *